US010694110B2

(12) United States Patent
Michishita et al.

(10) Patent No.: US 10,694,110 B2
(45) Date of Patent: Jun. 23, 2020

(54) IMAGE PROCESSING DEVICE, METHOD

(71) Applicant: SONY CORPORATION, Tokyo (JP)

(72) Inventors: Kenya Michishita, Chiba (JP); Yoshiaki Iwai, Tokyo (JP); Takeo Tsukamoto, Tokyo (JP)

(73) Assignee: SONY CORPORATION, Tokyo (JP)

( * ) Notice: Subject to any disclaimer, the term of this patent is extended or adjusted under 35 U.S.C. 154(b) by 122 days.

(21) Appl. No.: 16/073,957

(22) PCT Filed: Feb. 3, 2017

(86) PCT No.: PCT/JP2017/003940
§ 371 (c)(1),
(2) Date: Jul. 30, 2018

(87) PCT Pub. No.: WO2017/141730
PCT Pub. Date: Aug. 24, 2017

(65) Prior Publication Data
US 2019/0045100 A1 Feb. 7, 2019

(30) Foreign Application Priority Data
Feb. 18, 2016 (JP) .................................. 2016-028796

(51) Int. Cl.
*H04N 5/235* (2006.01)
*G06T 5/00* (2006.01)
(Continued)

(52) U.S. Cl.
CPC .......... *H04N 5/2351* (2013.01); *G06F 3/013* (2013.01); *G06T 5/001* (2013.01); *G06T 5/40* (2013.01);
(Continued)

(58) Field of Classification Search
CPC .......... H04N 5/2351; H04N 5/33; G06T 7/11; G06T 5/001; G06T 5/40; G06T 5/50; G06F 3/013
See application file for complete search history.

(56) References Cited

U.S. PATENT DOCUMENTS

2004/0005083 A1* 1/2004 Fujimura ........... G06K 9/00604
382/103
2004/0080623 A1* 4/2004 Cleveland ................ G06T 5/50
348/208.1
(Continued)

FOREIGN PATENT DOCUMENTS

JP 2014-064634 A 4/2014
JP 2016-049260 A 4/2016

OTHER PUBLICATIONS

International Search Report and Written Opinion of PCT Application No. PCT/JP2017/003940, dated Feb. 28, 2017, 05 pages of English Translation and 06 pages of ISRWO.
(Continued)

*Primary Examiner* — David F Dunphy
(74) *Attorney, Agent, or Firm* — Chip Law Group

(57) ABSTRACT

An image processing device includes an inward state detection unit that detects, on the basis of an inward image acquired by photographing of a user side, a state of outside light in the inward image as an inward outside light state, and an outward state detection unit that detects, on the basis of an outward image acquired by photographing of an opposite side of the user side, a state of outside light in the outward image as an outward outside light state. Also included is a control unit that performs brightness adjustment processing related to brightness of the inward image according to a detection result of the inward outside light state and a detection result of the outward outside light state, and a recognition processing unit that performs gaze detec-
(Continued)

tion of the user on the basis of the inward image acquired by performance of the brightness adjustment processing.

14 Claims, 8 Drawing Sheets

(51) Int. Cl.
*G06T 7/11* (2017.01)
*G06T 5/40* (2006.01)
*G06T 5/50* (2006.01)
*G06F 3/01* (2006.01)
*H04N 5/33* (2006.01)
*A61B 3/113* (2006.01)

(52) U.S. Cl.
CPC ............... *G06T 5/50* (2013.01); *G06T 7/11* (2017.01); *H04N 5/33* (2013.01); *A61B 3/113* (2013.01); *G06T 2207/20021* (2013.01)

(56) References Cited

U.S. PATENT DOCUMENTS

| | | | |
|---|---|---|---|
| 2008/0267600 A1* | 10/2008 | Omi | G06K 9/00255 396/14 |
| 2015/0365593 A1* | 12/2015 | Shinozaki | H04N 5/23232 348/207.1 |
| 2016/0063334 A1 | 3/2016 | Yasuda | |
| 2016/0116745 A1* | 4/2016 | Osterhout | G06F 3/03547 359/614 |
| 2016/0116979 A1* | 4/2016 | Border | G06F 3/013 345/156 |
| 2017/0068119 A1* | 3/2017 | Antaki | G06F 3/012 |
| 2019/0094981 A1* | 3/2019 | Bradski | G02B 30/26 |

OTHER PUBLICATIONS

International Preliminary Report on Patentability of PCT Application No. PCT/JP2017/003940, dated Aug. 30, 2018, 06 pages of English Translation and 05 pages of IPRP.

\* cited by examiner

IMAGE PROCESSING DEVICE, METHOD

CROSS REFERENCE TO RELATED APPLICATIONS

This application is a U.S. National Phase of International Patent Application No. PCT/JP2017/003940 filed on Feb. 3, 2017, which claims priority benefit of Japanese Patent Application No. JP 2016-028796 filed in the Japan Patent Office on Feb. 18, 2016. Each of the above-referenced applications is hereby incorporated herein by reference in its entirety.

TECHNICAL FIELD

The present technology relates to an image processing device, method, and program and specifically relates to an image processing device, method, and program in which an influence of outside light can be reduced.

BACKGROUND ART

Conventionally, a corneal reflex method of detecting a gaze by using an infrared (IR) ray is generally known as a method of performing gaze detection. In the corneal reflex method, an infrared ray is emitted and an image of an eye part of a user is photographed, and a gaze direction is detected from a positional relationship between a position of the infrared ray on the image acquired by the photographing, that is, a bright spot of the infrared ray and a pupil of a user to be detected.

Incidentally, in a case where gaze detection is performed in an environment with outside light, since sunlight as outside light includes an infrared component, there is a case where the outside light becomes a disturbance and influences the gaze detection.

Thus, in order to reduce an influence of a disturbance, a method of removing a disturbance component from an image photographed by emission of an infrared ray by using an image photographed in a state in which an infrared ray is not emitted has been proposed (see, for example, Patent Document 1).

CITATION LIST

Patent Document

Patent Document 1: Japanese Patent Application Laid-Open No. 2014-64634

SUMMARY OF THE INVENTION

Problems to be Solved by the Invention

However, in the above-described technology, it has been difficult to sufficiently reduce an influence of outside light.

For example, in a case where a disturbance component is removed by utilization of an image photographed in a state in which an infrared ray is not emitted, a time difference in photographing time is generated between photographing of an image in a state in which an infrared ray is not emitted and photographing of an image in a state in which an infrared ray is emitted.

Thus, for example, in a case where a photographing environment or a photographing direction varies in photographing of these images, a deviation is generated in a distribution of infrared ray components on the images. Thus, it becomes impossible to accurately remove a disturbance component. Also, in a case where there are much more outside light components than components of an emitted infrared ray, it is difficult to extract the components of the emitted infrared ray.

The present technology is provided in view of such a condition and is to make it possible to reduce an influence of outside light.

Solutions to Problems

An image processing device of an aspect of the present technology includes: an inward state detection unit that detects, on the basis of an inward image acquired by photographing of a user side, a state of outside light in the inward image as an inward outside light state; an outward state detection unit that detects, on the basis of an outward image acquired by photographing of an opposite side of the user side, a state of outside light in the outward image as an outward outside light state; a control unit that performs brightness adjustment processing related to brightness of the inward image according to a detection result of the inward outside light state and a detection result of the outward outside light state; and a recognition processing unit that performs gaze detection of the user on the basis of the inward image acquired by performance of the brightness adjustment processing.

In a case where a state of the outside light which state is indicated by the detection result of the inward outside light state and the detection result of the outward outside light state satisfies a first condition, the control unit can perform the brightness adjustment processing.

The control unit can change a photometric method in the brightness adjustment processing.

The control unit can change exposure time of the inward image in the brightness adjustment processing.

The control unit can change gain of gain adjustment processing performed with respect to the inward image in the brightness adjustment processing.

The inward image can be an infrared image, and one or a plurality of infrared ray transmission units that emits an infrared ray to the user can be further provided.

The control unit can change, in the brightness adjustment processing, an infrared ray transmission unit to be turned on.

The control unit can change, in the brightness adjustment processing, the number of infrared ray transmission units to be turned on.

The control unit can change, in the brightness adjustment processing, a quantity of an infrared ray emitted by the infrared ray transmission unit.

In a case where a state of the outside light which state is indicated by the detection result of the inward outside light state and the detection result of the outward outside light state satisfies a second condition, the control unit can perform gaze detection of the user on the basis of the outward image.

The recognition processing unit can perform iris recognition on the basis of the inward image.

The control unit can specify a glare region of the outside light in the inward image on the basis of the detection result of the inward outside light state and the detection result of the outward outside light state, and the recognition processing unit can perform the iris recognition while excluding the glare region from the inward image.

An image processing method or program of an aspect of the present technology includes the steps of: detecting, on the basis of an inward image acquired by photographing of a user side, a state of outside light in the inward image as an inward outside light state; detecting, on the basis of an outward image acquired by photographing of an opposite side of the user side, a state of outside light in the outward image as an outward outside light state; performing brightness adjustment processing related to brightness of the inward image according to a detection result of the inward outside light state and a detection result of the outward outside light state; and performing gaze detection of the user on the basis of the inward image acquired by performance of the brightness adjustment processing.

In an aspect of the present technology, a state of outside light in an inward image acquired by photographing of a user side is detected as an inward outside light state on the bases of the inward image, a state of outside light in an outward image acquired by photographing of an opposite side of the user side is detected as an outward outside light state on the basis of the outward image, brightness adjustment processing related to brightness of the inward image is performed according to a detection result of the inward outside light state and a detection result of the outward outside light state, and gaze detection of the user is performed on the basis of the inward image acquired by performance of the brightness adjustment processing.

Effects of the Invention

According to an aspect of the present technology, it is possible to further reduce an influence of outside light.

Note that an effect described herein is not necessarily limited and may be any of the effects described in the present disclosure.

MODE FOR CARRYING OUT THE INVENTION

In the following, an embodiment to which the present technology is applied will be described with reference to the drawings.

First Embodiment

<Configuration Example of Image Processing Device>

The present technology is to make it possible in an image processing device attachable to a head of a user to detect an outside light state on an environment side, that is, an outward side and an outside light state on a user side, that is, an inward side and to further reduce an influence of outside light in processing using an image such as gaze detection or iris recognition by using detection results of these two outside light states.

Figure 1:
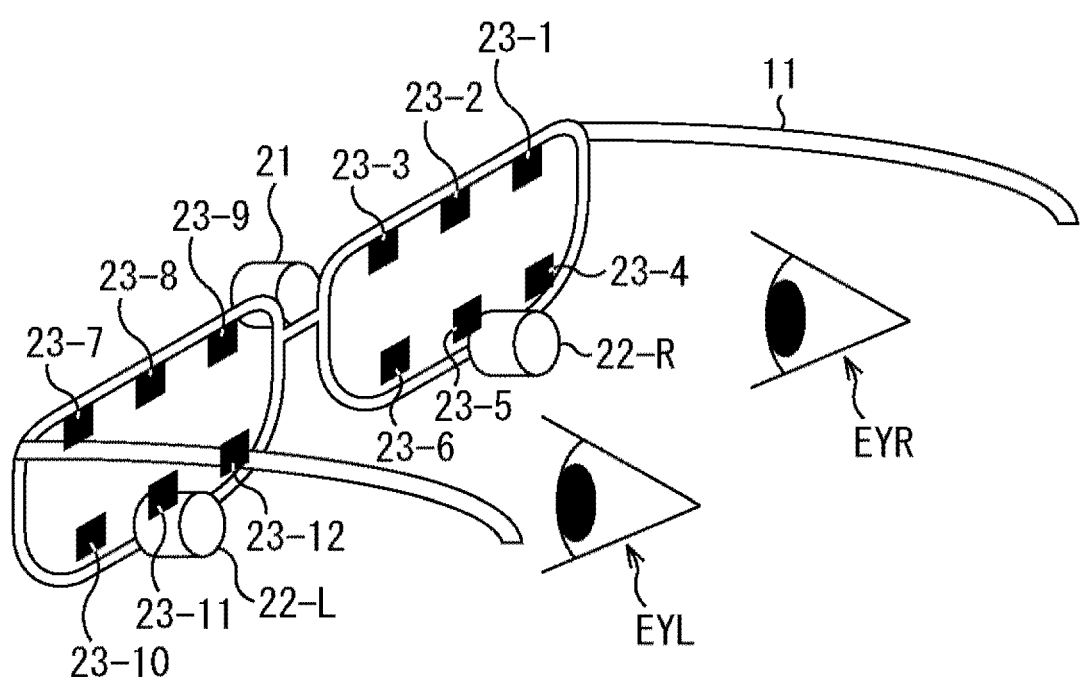
FIG. 1 is a view illustrating a configuration example of an image processing device.

FIG. 1 is a view illustrating a configuration example of an embodiment of an image processing device to which the present technology is applied.

The image processing device 11 illustrated in FIG. 1 is a glasses-type wearable device that can be attached to a head of a user. In this example, the user sees an image displayed on a lens part of the attached image processing device 11 or an outside environment through the lens part with a right eye EYR and a left eye EYL.

Note that in the following, a user side in relation to the image processing device 11, more specifically, a side of the right eye EYR and the left eye EYL of the user with respect to the lens of the image processing device 11 will be also simply referred to as a user side or an inner side. Also, an opposite side of the user side in relation to the image processing device 11, that is, an environment side will be also referred to as an outer side. Moreover, in the following, light other than an infrared ray emitted by the image processing device 11 to the user, that is, environmental light such as sunlight will be referred to as outside light.

The image processing device 11 performs iris recognition or gaze detection with respect to a user, or executes various application programs by using a result of the gaze detection, or the like.

Also, the image processing device 11 includes an outward camera 21 to photograph an image on the outer side, and an inward camera 22-R and an inward camera 22-L to photograph an image on the inner side. Moreover, an infrared ray transmission unit 23-1 to an infrared ray transmission unit 23-12 that emit infrared rays to the right eye EYR and the left eye EYL of the user are also provided toward the inner side in the image processing device 11.

Note that in the following, in a case where it is not necessary to specifically distinguish the inward camera 22-R and the inward camera 22-L, these will be also simply referred to as an inward camera 22. Also, in the following, in a case where it is not necessary to specifically distinguish the infrared ray transmission unit 23-1 to the infrared ray transmission unit 23-12, these will be also simply referred to as an infrared ray transmission unit 23.

The outward camera 21 includes an imaging element such as a complementary metal oxide semiconductor (CMOS) image sensor and photographs a visible light image of an object on the outer side. In the following, a visible light image photographed by the outward camera 21 will be also specifically referred to as an outward image.

Each of the inward camera 22-R and the inward camera 22-L is an infrared camera including an imaging element such as a CMOS image sensor, and photographs an image of an infrared ray, that is, an infrared image in a region including the right eye EYR and a region including the left eye EYL of the user on the inner side. In the following, the image of an infrared ray which image is photographed by the inward camera 22 will be also specifically referred to as an inward image.

Each of the infrared ray transmission unit 23-1 to the infrared ray transmission unit 23-12 includes, for example, a light emitting diode (LED) or the like, and emits an infrared ray to a part of the right eye EYR and the left eye EYL of the user on the inner side. Specifically, in this example, six infrared ray transmission unit 23-1 to infrared ray transmission unit 23-6 are provided in such a manner as to surround an outer periphery of a lens facing the right eye EYR of the user. Similarly, six infrared ray transmission unit 23-7 to infrared ray transmission unit 23-12 are provided in such a manner as to surround an outer periphery of a lens facing the left eye EYL of the user.

Thus, an inward image includes a component of an infrared ray emitted by these infrared ray transmission units 23, and an infrared ray component in outside light emitted to an eye part of the user. The infrared ray transmission units 23 are used for gaze detection of the user by a corneal reflex method.

<Gaze Detection and Iris Recognition>

In the image processing device 11, gaze detection or iris recognition is performed on the basis of an inward image. Here, the outward camera 21 and the inward camera 22 are used to detect a state of outside light, and the gaze detection or the iris recognition is performed on the basis of a result of the detection.

For example, in detection of a state of outside light (hereinafter, referred to as outside light state), an outside light state is detected by utilization of the outward camera 21 and an outside light state is detected by utilization of the inward camera 22. In the following, in order to distinguish these outside light states, the outside light state detected by utilization of the outward camera 21 will be also specifically referred to as an outward outside light state and the outside light state detected by utilization of the inward camera 22 will be also specifically referred to as an inward outside light state.

Here, the outside light state means a state related to brightness of an outside light component in each region on an image and is, for example, a distribution of an outside light component on an image.

On the basis of a detection result of the outward outside light state and a detection result of the inward outside light state, the image processing device 11 performs gaze detection while arbitrarily performing control related to emission of an infrared ray, exposure control, a gain adjustment, or the like as brightness adjustment processing.

Figure 2:
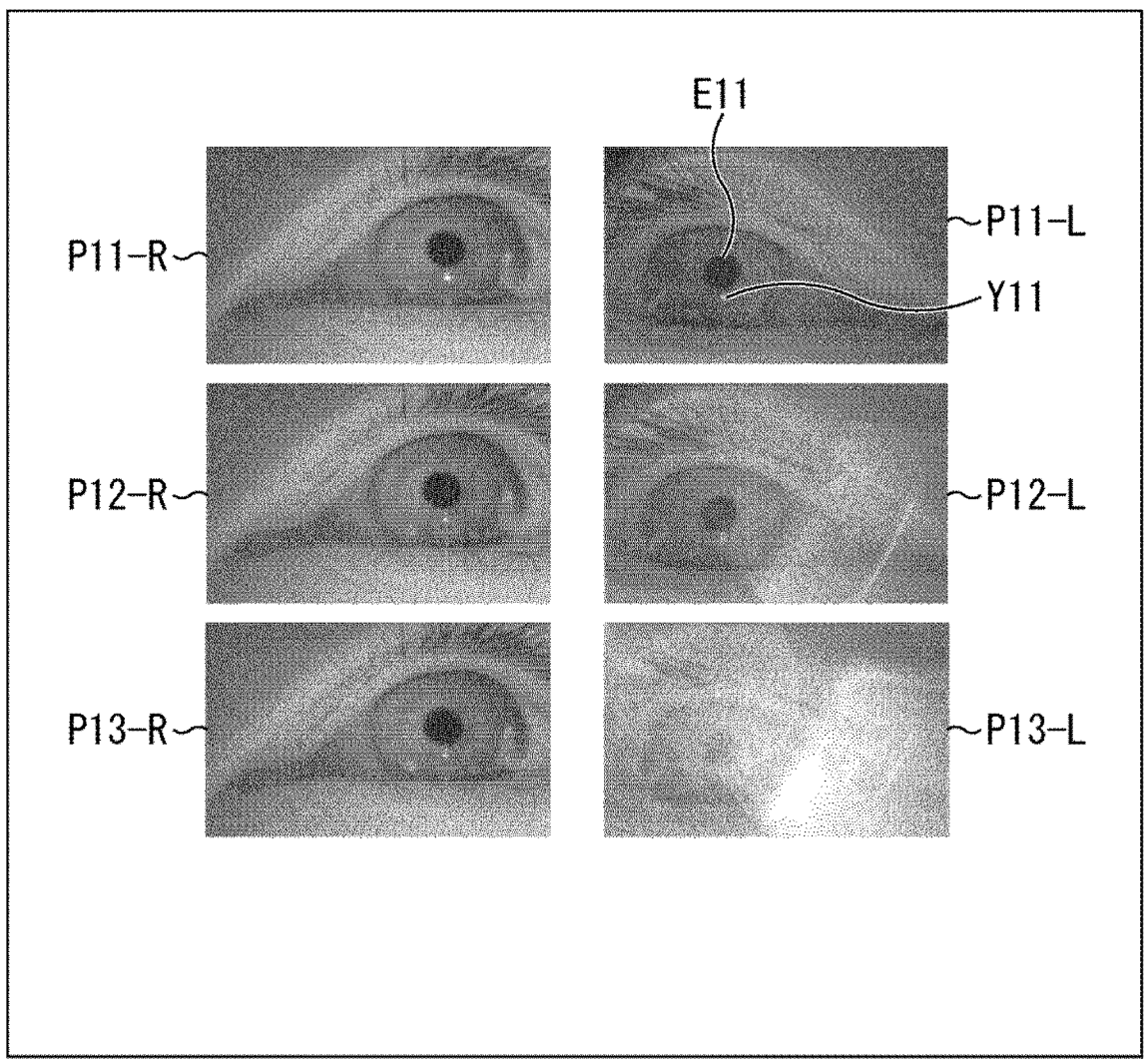
FIG. 2 is a view for describing an outside light state level and gaze detection.

For example, in gaze detection or iris recognition, the image processing device 11 detects, as the inward outside light state, an outside light state level in an inward image which level indicates an influence degree of an outside light component with respect to the gaze detection or the iris recognition, as illustrated in FIG. 2.

For example, as illustrated in FIG. 2, it is assumed that an inward image P11-R and an inward image P11-L are acquired as inward images photographed at certain time.

Here, the inward image P11-R and the inward image P11-L are respectively images photographed by the inward camera 22-R and the inward camera 22-L. In the following, in a case where it is not necessary to specifically distinguish the inward image P11-R and the inward image P11-L, these will be also simply referred to as an inward image P11.

Also, it is assumed that an inward image P12-R and an inward image P12-L, and an inward image P13-R and an inward image P13-L are photographed at time different from that of the inward images P11.

Here, the inward image P12-R and the inward image P12-L are respectively images photographed by the inward camera 22-R and the inward camera 22-L, and the inward image P13-R and the inward image P13-L are respectively images photographed by the inward camera 22-R and the inward camera 22-L.

In the following, in a case where it is not necessary to specifically distinguish the inward image P12-R and the inward image P12-L, these will be also simply referred to as an inward image P12. Also, in a case where it is not necessary to specifically distinguish the inward image P13-R and the inward image P13-L, these will be also simply referred to as an inward image P13. The inward image P11 to inward image P13 are images photographed at different time.

An eye part of the user is clearly reflected on the inward image P11. Gaze detection or iris recognition can be sufficiently performed by utilization of such an inward image P11. For example, a pupil E11 of the user and an infrared ray emitted (transmitted) by a predetermined infrared ray transmission unit 23, that is, a bright spot Y11 of the infrared ray are reflected on the inward image P11-L. It is possible to detect a gaze direction of the user from a positional relationship of these pupil E11 and bright spot Y11.

In a case of a state in which an influence of outside light is not generated, that is, a state in which a pupil or iris, and a bright spot of an infrared ray are sufficiently clearly reflected, the image processing device 11 determines that an outside light state level indicating an influence degree of an outside light component is a level L0.

Also, for example, a pupil and a bright spot of an infrared ray are reflected sufficiently clearly on the inward image P12-R with little influence of outside light. However, reflection light is reflected in a lower right part in the drawing and it is difficult to see a bright spot of an infrared ray in the inward image P12-L.

Thus, if the inward image P12-L is used as it is, it is difficult to perform correct gaze detection. It becomes necessary to perform exposure control, a gain adjustment, emission control of an infrared ray such as an adjustment of a light quantity or a modification of an emission position of an infrared ray, or the like in such a manner that a bright spot of an infrared ray, a pupil, and an iris becomes clearer.

In a case of a state in which an influence of outside light can be reduced to a sufficient degree by some kind of processing such as the state of the inward image P12, that is, in a case of a state in which there is a possibility that gaze detection or iris recognition can be performed by exposure control, a gain adjustment, emission control of an infrared ray, or the like, the image processing device 11 determines that an outside light state level indicating an influence degree of an outside light component is a level L1.

Moreover, for example, a pupil and a bright spot of an infrared ray are reflected sufficiently clearly on the inward image P13-R with little influence of outside light. However, reflection light is significantly reflected in a lower right part in the drawing and a bright spot of an infrared ray and an iris are hardly seen in the inward image P13-L. In this case, it is difficult to perform gaze detection or iris recognition even if exposure control, a gain adjustment, or emission control of an infrared ray is performed.

In a case where it is difficult to perform gaze detection or iris recognition by exposure control, a gain adjustment, or emission control of an infrared ray such as the case of the inward image P13, the image processing device 11 determines that an outside light state level indicating an influence degree of an outside light component is a level L2.

The image processing device 11 performs processing of gaze detection or iris recognition by using an outside light state level as an inward outside light state detected in such a manner on the basis of an inward image.

Figure 3:
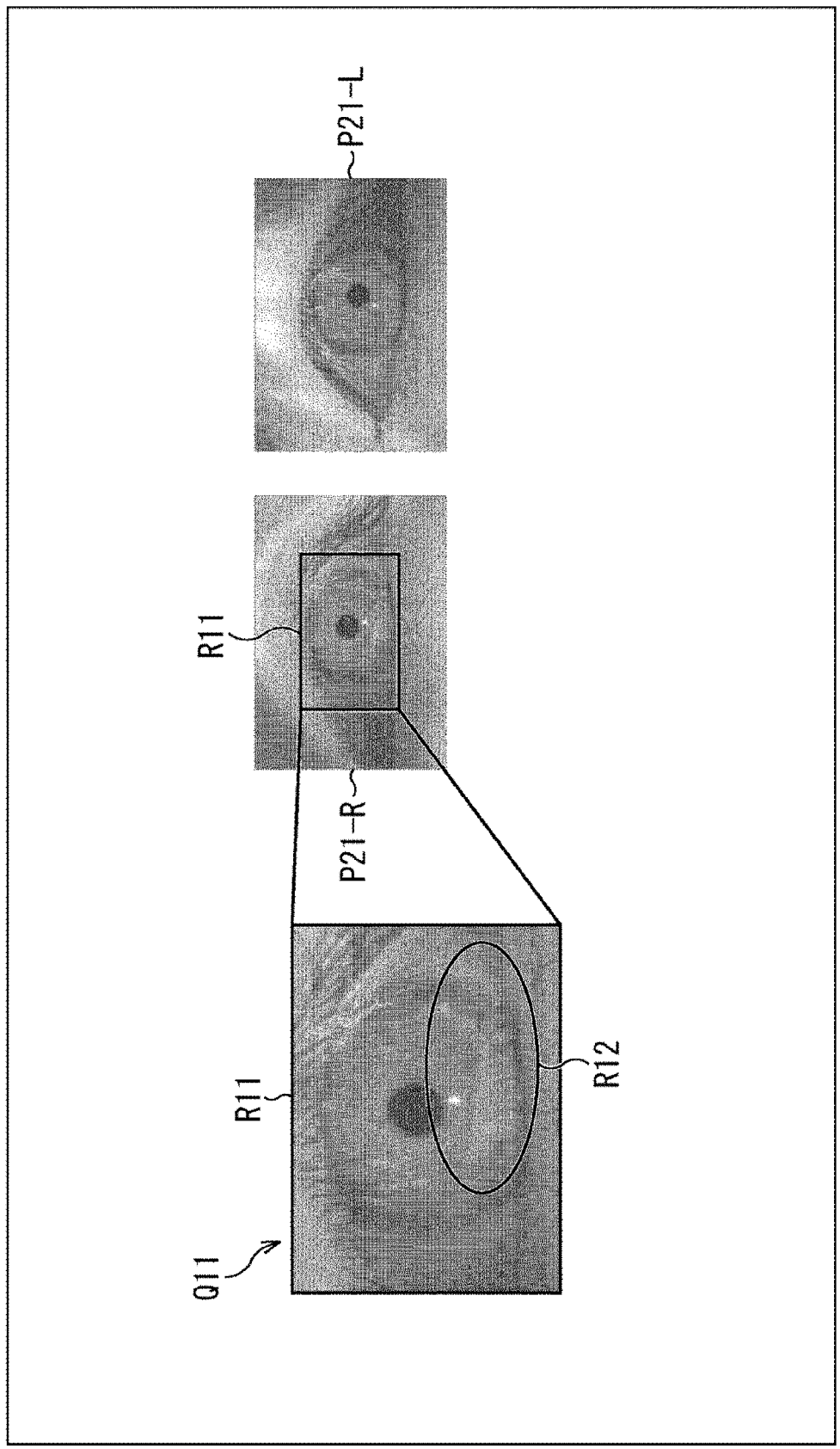
FIG. 3 is a view for describing a glare and iris recognition.

Moreover, in iris recognition, a glare region that is a region in which a glare of outside light is generated as illustrated, for example, in FIG. 3 is specified and processing of the iris recognition is performed by utilization of a result of the specification in addition to the detection result of the inward outside light state and the detection result of the outward outside light state.

In FIG. 3, a glare by outside light is generated in a partial region of an inward image P21-R that is one of the inward image P21-R and an inward image P21-L acquired by photographing.

Here, the inward image P21-R and the inward image P21-L are respectively images photographed by the inward camera 22-R and the inward camera 22-L. In the following, in a case where it is not necessary to specifically distinguish the inward image P21-R and the inward image P21-L, these will be also simply referred to as an inward image P21.

In this example, most of iris parts are clearly reflected on the inward images P21. However, a glare is generated in a region including the iris part in the inward image P21-R. Here, a drawing indicated by an arrow Q11 is a view in which a part of a region R11 in the inward image P21-R is enlarged and displayed. As it is understood from the drawing indicated by the arrow Q11, a glare by outside light is generated in a lower side in the drawing, that is, a part of a region R12 in the iris part of the eye of the user.

In a case where a glare is generated in an iris part in such a manner, it is difficult to correctly perform iris recognition in the part by image recognition or the like.

Thus, in the image processing device 11, iris recognition is performed while such a glare region is removed, that is, excluded from a region to be processed. With this arrangement, it is possible to reduce an influence of outside light and to more correctly perform iris recognition even in a case where outside light is intense and a glare is generated.

Figure 4:
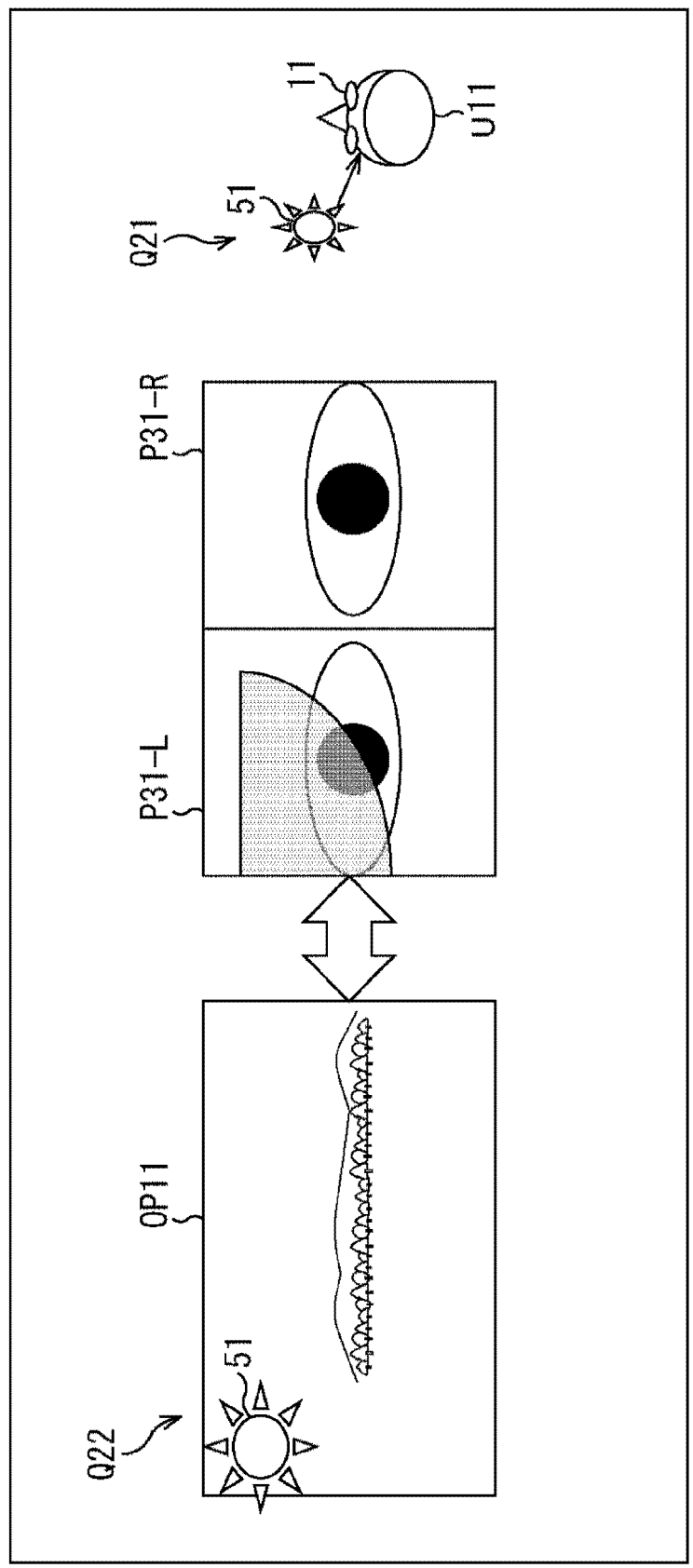
FIG. 4 is a view for describing a correlation between an inward image and an outward image.

Also, in the image processing device 11, in a case where a glare region is specified or it is determined whether to perform exposure control, a gain adjustment, or emission control of an infrared ray, a correlation between an outward image and an inward image is used as illustrated, for example, in FIG. 4.

That is, for example, it is assumed that a user U11 wears the image processing device 11 and the sun 51 that is a light source of outside light is ahead of the user U11 on the left as indicated by an arrow Q21 in FIG. 4.

In such a case, for example, an outward image OP11, an inward image P31-R, and an inward image P31-L are acquired as indicated by an arrow Q22.

Here, the inward image P31-R and the inward image P31-L are respectively images photographed by the inward camera 22-R and the inward camera 22-L. In the following, in a case where it is not necessary to specifically distinguish the inward image P31-R and the inward image P31-L, these will be also simply referred to as an inward image P31.

In this example, since the sun 51 is ahead of the user U11 on the left, the sun 51 is reflected as an object on an upper left side in the drawing of the outward image OP11 and luminance in the vicinity thereof is high.

Also, luminance on an upper left side in the drawing of the inward image P31-L photographed by the inward camera 22-L on a side of the sun 51 in relation to the user U11 is high in the inward images P31 due to an influence of the sun 51. This is because intense light from the sun 51, that is, outside light is reflected in the vicinity of a left eye of the user U11, a temple part of the image processing device 11, or the like and is reflected on the inward image P31-L.

In such a manner, by comparison between the outward image OP11 and the inward images P31, it can be understood that there is a correlation in a distribution of brightness (luminance) thereof.

Thus, for example, in a case where there is a region with high luminance in the outward image OP11, it can be estimated that luminance becomes also high in a region of the inward images P31 which region corresponds to the region. By using such a correlation between the outward image OP11 and the inward images P31, it is possible to determine, for example, whether a glare is generated in the inward images P31 or to specify a region in which the glare is generated, and it becomes possible to more appropriately perform gaze detection or iris recognition.

<Functional Configuration Example of Image Processing Device>

Figure 5:
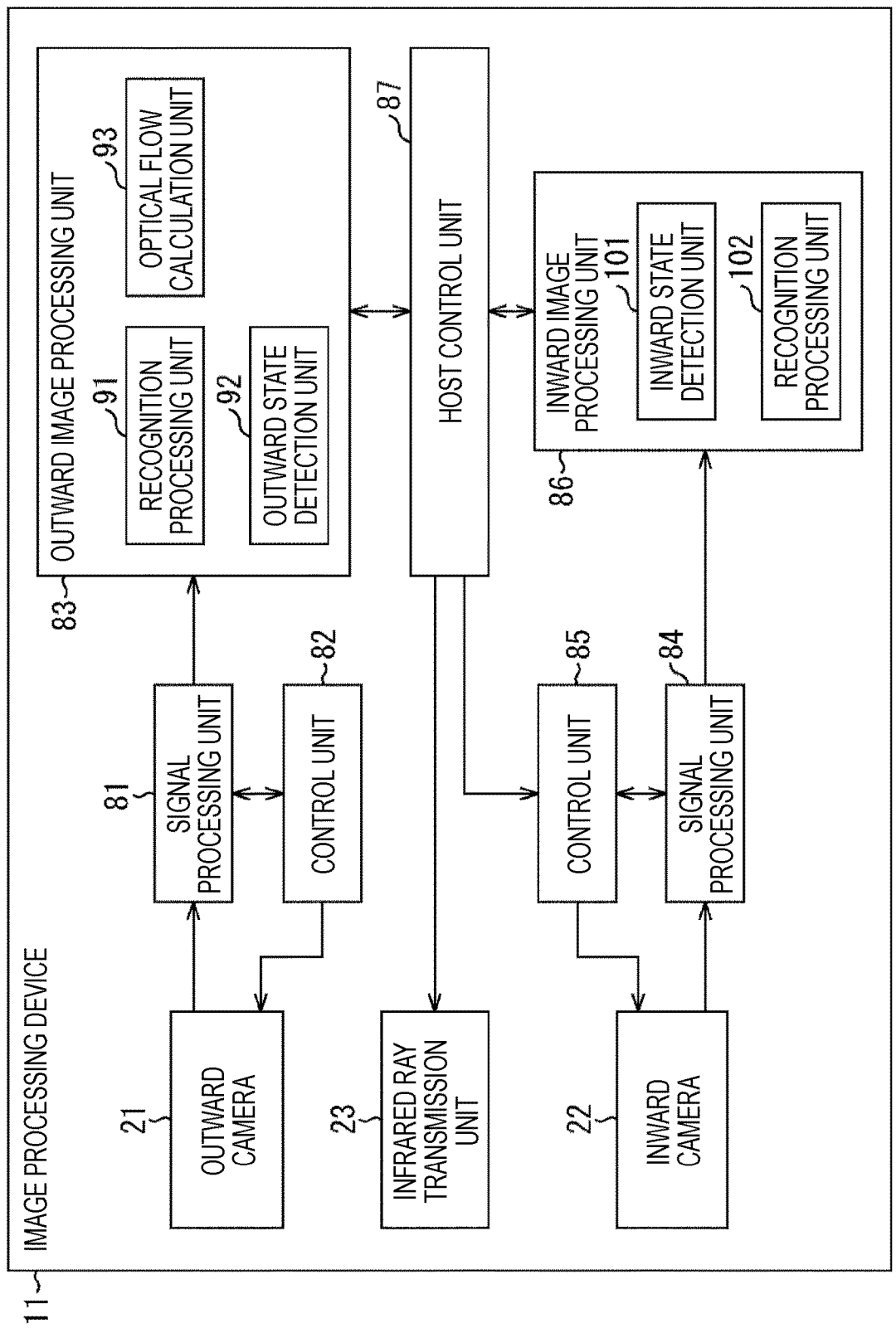
FIG. 5 is a view illustrating a functional configuration example of the image processing device.

Next, a functional configuration example of the image processing device 11 illustrated in FIG. 1 will be described. FIG. 5 is a block diagram illustrating a functional configuration example of the image processing device 11. Note that in FIG. 5, the same sign is assigned to a part corresponding to that in a case of FIG. 1 and a description thereof is arbitrarily omitted.

The image processing device 11 illustrated in FIG. 5 includes an outward camera 21, a signal processing unit 81, a control unit 82, an outward image processing unit 83, an inward camera 22, an infrared ray transmission unit 23, a signal processing unit 84, a control unit 85, an inward image processing unit 86, and a host control unit 87.

The signal processing unit 81 performs various kinds of image processing such as demosaic processing, gain adjustment processing, contrast adjustment processing, and format conversion processing with respect to an outward image supplied by the outward camera 21 and supplies this to the outward image processing unit 83. The control unit 82 controls photographing performed by the outward camera 21, or controls image processing performed by the signal processing unit 81. The control unit 82 exchanges various kinds of information with the signal processing unit 81 if necessary.

The outward image processing unit 83 performs detection of an outward outside light state, or the like on the basis of an outward image supplied by the signal processing unit 81. The outward image processing unit 83 includes a recognition processing unit 91, an outward state detection unit 92, and an optical flow calculation unit 93.

For example, the recognition processing unit 91 performs object recognition with respect to an outward image, and calculates a distance from the image processing device 11 to an object placed on a front side of the image processing device 11. Such measurement of a distance to an object by object recognition is executed, for example, as processing of an application program executed by the image processing device 11.

The outward state detection unit 92 detects an outward outside light state on the basis of an outward image supplied by the signal processing unit 81 and supplies a result of the detection to the host control unit 87.

The optical flow calculation unit 93 calculates an optical flow on the basis of an outward image supplied by the signal processing unit 81 and supplies a result of the calculation to the host control unit 87. This optical flow is used to detect a gaze direction of a user in a case where an outside light state satisfies a predetermined condition such as a case where an outside light state level is the level L2, that is, in a case where gaze detection using an inward image is difficult.

The signal processing unit 84 performs various kinds of image processing such as gain adjustment processing, contrast adjustment processing, and format conversion processing with respect to an inward image supplied by the inward camera 22 and supplies this to the inward image processing unit 86. The control unit 85 controls photographing by the inward camera 22 or controls image processing by the signal processing unit 84 according to control by the host control unit 87. The control unit 85 exchanges various kinds of information with the signal processing unit 84 if necessary.

The inward image processing unit 86 performs detection of an inward outside light state, or the like on the basis of an inward image supplied by the signal processing unit 84. The inward image processing unit 86 includes an inward state detection unit 101 and a recognition processing unit 102.

The inward state detection unit 101 detects an inward outside light state on the basis of an inward image supplied by the signal processing unit 84 and supplies a result of the detection to the host control unit 87. The recognition processing unit 102 performs gaze detection or iris recognition on the basis of an inward image supplied by the signal processing unit 84.

The host control unit 87 controls an operation of the whole image processing device 11. For example, the host control unit 87 controls the infrared ray transmission unit 23 or the control unit 85 according to a detection result of an inward outside light state and a detection result of an outward outside light state, and performs brightness adjustment processing related to brightness of an inward image.

<Description of Iris Recognition Processing>

Next, processing performed by the image processing device 11 will be described.

First, iris recognition processing performed by the image processing device 11 will be described with reference to a flowchart in FIG. 6. This iris recognition processing is performed, for example, when a user wears the image processing device 11, execution of iris recognition is instructed by operation of the image processing device 11 by the user, or the like.

The outward camera 21 and the inward camera 22 start photographing in step S11.

That is, the outward camera 21 photographs an outward image according to control by the control unit 82, and serially supplies an outward image acquired by the photographing to the signal processing unit 81. Also, the signal processing unit 81 performs various kinds of image processing such as demosaic processing, gain adjustment processing, contrast adjustment processing, and format conversion processing with respect to the outward image supplied by the outward camera 21 and supplies this to the outward image processing unit 83.

Also, the inward camera 22 photographs an inward image according to control by the control unit 85, and serially supplies an inward image acquired by the photographing to the signal processing unit 84. Also, the signal processing unit 84 performs various kinds of image processing such as gain adjustment processing, contrast adjustment processing, and format conversion processing with respect to the inward image supplied by the inward camera 22 and supplies this to the inward image processing unit 86. Note that in the iris recognition processing, emission of an infrared ray by the infrared ray transmission unit 23 is not performed.

In step S12, the image processing device 11 performs correlation processing for iris recognition.

For example, the outward state detection unit 92 divides an outward image supplied by the signal processing unit 81 into a plurality of divided regions, and generates a histogram of a luminance value (pixel value), that is, a histogram of brightness of each of the divided regions. Then, the outward state detection unit 92 supplies, as a detection result of an outward outside light state, information including a generated histogram of each of the divided regions to the host control unit 87.

The information that includes the histogram of each of the divided regions of the outward image and that is acquired in such a manner is information indicating a luminance distribution (distribution of brightness) in each region in the outward image. In the following, the information including the histogram of each of the divided regions of the outward image will be also referred to as an outward brightness map.

Also, the inward state detection unit 101 divides an inward image supplied by the signal processing unit 84 into a plurality of divided regions and generates a histogram of a luminance value of each of the divided regions. Then, the inward state detection unit 101 supplies, as a detection result of an inward outside light state, information including the generated histogram of each of the divided regions to the host control unit 87.

The information that includes the histogram of each of the divided regions of the inward image and that is acquired in such a manner is information indicating a luminance distribution of each region in the inward image. In the following, the information including the histogram of each of the divided regions of the inward image will be also referred to as an inward brightness map.

Note that in a case where an outward image and an inward image are divided into a plurality of divided regions, these images may be divided into divided regions having the same size or may be divided into divided regions having different sizes depending on a region. In this case, for example, since an eye part of a user is reflected as an object in an inward image, a region in which an iris part of the eye of the user is likely to be reflected may be divided into divided regions smaller than the other regions.

Moreover, the host control unit 87 associates the outward brightness map supplied by the outward state detection unit 92 and the inward brightness map supplied by the inward state detection unit 101 and holds these as correlation information for iris recognition. The correlation information for iris recognition which information is acquired in such a manner is information indicating a correlation between brightness of the outward image and that of the inward image.

Also, from the correlation information for iris recognition and a structure of a glasses-type wearable device as the image processing device 11, the host control unit 87 specifies, in the inward image, an estimated glare region that is a region where it is estimated that a glare of outside light is generated, and holds a result of the specification as estimated glare region information.

For example, the host control unit 87 specifies, in the outward brightness map included in the correlation information for iris recognition, a region that is significantly bright, that is, has significantly high luminance compared to a surrounding divided region.

More specifically, for example, a divided region in which, compared to histograms of the other divided regions, luminance (level) having the maximum frequency value is high for a predetermined value or more or a width of a luminance distribution, that is, a width in a luminance (level) direction of a part having a large frequency value is wide is specified as a region with high luminance.

Also, for example, in a case where a difference between an average value or a representative value of luminance in all divided regions or surrounding divided regions and an average value or a representative value of luminance in a predetermined divided region becomes equal to or larger than a threshold, the predetermined divided region may be specified as a region with significantly high luminance.

From a region with significantly high luminance in an outward image and a structure of the image processing device 11, the host control unit 87 specifies a divided region in which a glare is likely to be generated in an inward image, and sets the divided region as a candidate of an estimated glare region.

Moreover, the host control unit 87 compares a histogram of a candidate region of the estimated glare region and a histogram of a surrounding divided region of the candidate region in the inward brightness map included in the correlation information for iris recognition, and specifies a final estimated glare region on the basis of a result of the comparison. For example, in a case where a candidate region is brighter than a surrounding divided region or a luminance distribution indicated by a histogram of the candidate region is different from a luminance distribution in the surrounding divided region, the candidate region is specified as an estimated glare region.

Here, for example, a luminance distribution being different means that luminance (level) with the maximum frequency value is different or a width in a luminance direction of a part with a large frequency value is wide compared to a histogram of a surrounding divided region.

Note that since an eye part of the user is mainly reflected as an object on the inward image, it is possible to previously predict a pattern of a luminance distribution of the eye part. Thus, an estimated pattern of a luminance distribution, that is, an estimated histogram of each of the divided regions may be held as a reference pattern, and an estimated glare region may be finally specified by comparison between an actual histogram of a candidate region of an estimated glare region, and a histogram of a divided region of a reference pattern at the same position with the candidate region. Also, an estimated glare region may be specified by comparison between a reference pattern and an inward brightness map.

It can be said that the correlation processing for iris recognition in which such correlation information for iris recognition or estimated glare region information is calculated and held is processing of performing calibration for detection of an outside light state. In the following, correlation information for iris recognition is used as calibration information indicating an initial state. More specifically, for example, the correlation processing for iris recognition is performed at timing at which a user wears the image processing device 11.

After the correlation processing for iris recognition is performed, processing of step S13 is performed at timing at which iris recognition is performed. That is, in step S13, the outward state detection unit 92 detects an outward outside light state on the basis of an outward image supplied by the signal processing unit 81 and supplies a result of the detection to the host control unit 87.

For example, similarly to a case in step S12, the outward state detection unit 92 generates an outward brightness map by generating a histogram of a luminance value in each of a plurality of divided regions in the outward image, and sets the acquired outward brightness map as a detection result of an outward outside light state. Here, a method of dividing an outward image into a plurality of divided regions is similar to that in the case of step S12.

The outward brightness map acquired in such a manner is information indicating a state of outside light in the outward image.

In step S14, the inward state detection unit 101 detects an inward outside light state on the basis of an inward image supplied by the signal processing unit 84.

For example, similarly to the case in step S12, the inward state detection unit 101 generates an inward brightness map by generating a histogram of a luminance value in each of a plurality of divided regions of the inward image. Here, a method of dividing an inward image into a plurality of divided regions is similar to that in the case of step S12. The inward brightness map acquired in such a manner is information indicating a state of outside light in the inward image.

Also, the inward state detection unit 101 determines an outside light state level of the inward image on the basis of the inward brightness map.

For example, the inward state detection unit 101 previously holds an inward brightness map in a state in which there is no outside light, and calculates an influence degree of outside light with respect to iris recognition or gaze detection by comparing the previously held inward brightness map and the generated inward brightness map.

For example, an influence degree of outside light is calculated in each divided region on the basis of a difference in an average value or a representative value of a luminance value, a difference in a frequency value of each bin, or the like in divided regions at the same positions in the previously held inward brightness map and the generated inward brightness map. Then, an influence degree in the whole inward image is calculated as a final influence degree of outside light on the basis of an influence degree acquired for each divided region. Here, weighting or the like may be performed according to a position of a divided region. It can be said that the influence degree calculated in such a manner is calculated from a luminance distribution, that is, a pattern of luminance indicated by the inward brightness map.

The inward state detection unit 101 specifies a current outside light state level by comparing the influence degree of outside light calculated in such a manner and a previously set threshold, that is, by performing threshold processing with respect to the influence degree.

The inward state detection unit 101 supplies, as a detection result of an inward outside light state, the inward brightness map and the outside light state level acquired in such a manner to the host control unit 87.

In step S15, the host control unit 87 determines whether iris recognition is possible on the basis of the detection result of the inward outside light state which result is supplied by the inward state detection unit 101.

For example, the host control unit 87 determines that the iris recognition is possible in a case where the outside light state level supplied as the detection result of the inward outside light state is the level L0.

Here, for example, the iris recognition can be normally performed in a case where the outside light state level is the level L0. However, in a case where the outside light state level is the level L1 or the level L2, it is determined that the iris recognition cannot be performed accurately since the outside light is intense.

Note that it may be determined whether the iris recognition is possible according to whether an outside light state indicated by a detection result of each of an inward outside light state and an outward outside light state satisfies a predetermined condition, that is, whether the predetermined condition is satisfied by the detection result of each of the inward outside light state and the outward outside light state.

In a case where it is determined in step S15 that the iris recognition is not possible, the iris recognition is not performed and the iris recognition processing is ended. In this case, for example, the host control unit 87 may output information indicating that the iris recognition cannot be performed to a higher control unit, and the information may be displayed on a display unit provided in a superimposed manner on a lens part of the image processing device 11.

On the other hand, in a case where it is determined in step S15 that the iris recognition is possible, the host control unit 87 determines in step S16 whether there is a glare of outside light in the inward image.

For example, the host control unit 87 determines whether there is a glare on the basis of the held correlation information for iris recognition and estimated glare region information, the outward brightness map as the detection result of the outward outside light state supplied in the processing of step S13, and the inward brightness map as the detection result of the inward outside light state supplied in the processing of step S14.

More specifically, for example, the host control unit 87 detects an abnormal region different from a surrounding region from the outward brightness map acquired in step S13 and the inward brightness map acquired in the processing of step S14.

Here, the abnormal region is, for example, a divided region in which luminance (level) with the maximum frequency value is large for a predetermined value or more or a width of a luminance distribution, that is, a width in a luminance (level) direction in a part with a large frequency value is wide compared to a histogram of a surrounding divided region. Also, for example, a region in which an average value or a representative value of a luminance value in a divided region becomes equal to or larger than a threshold may be an abnormal region.

The host control unit 87 determines whether there is a correlation between an abnormal region detected from the outward brightness map and an abnormal region detected from the inward brightness map.

Here, the abnormal region detected from the outward brightness map is referred to as a detection region OR, and the abnormal region detected from the inward brightness map is referred to as a detection region IR.

The host control unit 87 determines that there is a correlation in a case where a region OT at the same position with the detection region OR in the outward brightness map included in the correlation information for iris recognition is a region that is bright compared to a surrounding region or that has a luminance distribution different therefrom, and a region IT at the same position with the detection region IR in the inward brightness map included in the correlation information for iris recognition is a region that is bright compared to a surrounding region or that has a luminance distribution different therefrom.

The determination whether there is a correlation is performed in such a manner on the basis of whether there is a correlation with respect to a position and a luminance distribution of the detection region OR and those of the detection region IR.

Moreover, in a case where the detection region IR determined to have a correlation with the detection region OR is a region at the same position with a region indicated by the held estimated glare region information, the host control unit 87 determines that the detection region IR is a glare region of outside light.

In such a manner, it is possible to accurately specify a glare region even in a state in which outside light is not that intense by detecting the glare region by using correlation information for iris recognition which information indicates a correlation between an outward image and an inward image, or estimated glare region information.

Note that in a case where the above-described reference pattern is previously held, a glare region may be detected by utilization of the reference pattern.

In such a case, for example, the host control unit 87 specifies a divided region with a luminance distribution different from a previously held reference pattern by comparing the previously held reference pattern with a histogram of each divided region of an inward image that is actually detected as an inward outside light state. Then, in a case where the specified divided region is a region at the same position with a region indicated by estimated glare region information, the host control unit 87 determines that the specified region is a glare region.

Here, in a case where there is a correlation between a detection result of the outward outside light state and a detection result of the inward outside light state from the correlation information for iris recognition, the specified region may be finally determined to be a glare region.

In a case where a glare region is detected from an inward image in the above manner, it is determined in step S16 that there is a glare.

In a case where it is determined in step S16 that there is a glare, the host control unit 87 supplies information indicating a glare region to the recognition processing unit 102, and the processing goes to step S17.

In step S17, the recognition processing unit 102 removes the glare region indicated by the information supplied by the host control unit 87 from the inward image supplied by the signal processing unit 84, and performs iris recognition.

For example, the recognition processing unit 102 removes the glare region from the inward image, and performs iris recognition with respect to a remaining region of the inward image by pattern recognition using a previously held dictionary or the like including a feature amount or the like. By performing iris recognition while excluding the glare region in the inward image from an object of processing in such a manner, it is possible to reduce an influence of outside light and to more correctly perform iris recognition. After performing the iris recognition, the recognition processing unit 102 outputs a result of the recognition, and the iris recognition processing is ended.

On the other hand, in a case where it is determined in step S16 that there is no glare, the host control unit 87 supplies information indicating that there is no glare to the recognition processing unit 102, and the processing goes to step S18.

In step S18, the recognition processing unit 102 performs iris recognition on the basis of the inward image supplied by the signal processing unit 84.

For example, according to the information which indicates that there is no glare and which is supplied by the host control unit 87, the recognition processing unit 102 performs iris recognition with the whole inward image as an object of processing by pattern recognition using a previously held dictionary or the like including a feature amount or the like. After performing the iris recognition, the recognition processing unit 102 outputs a result of the recognition, and the iris recognition processing is ended.

In the above manner, by using the detection results of the outward outside light state and the inward outside light state, the image processing device 11 specifies whether there is a glare of outside light in the inward image, excludes a glare region from the inward image in a case where there is a glare, and performs iris recognition. With this arrangement, it is possible to reduce an influence of outside light and to more correctly perform iris recognition.

<Description of Gaze Detection Processing>

Figure 7:
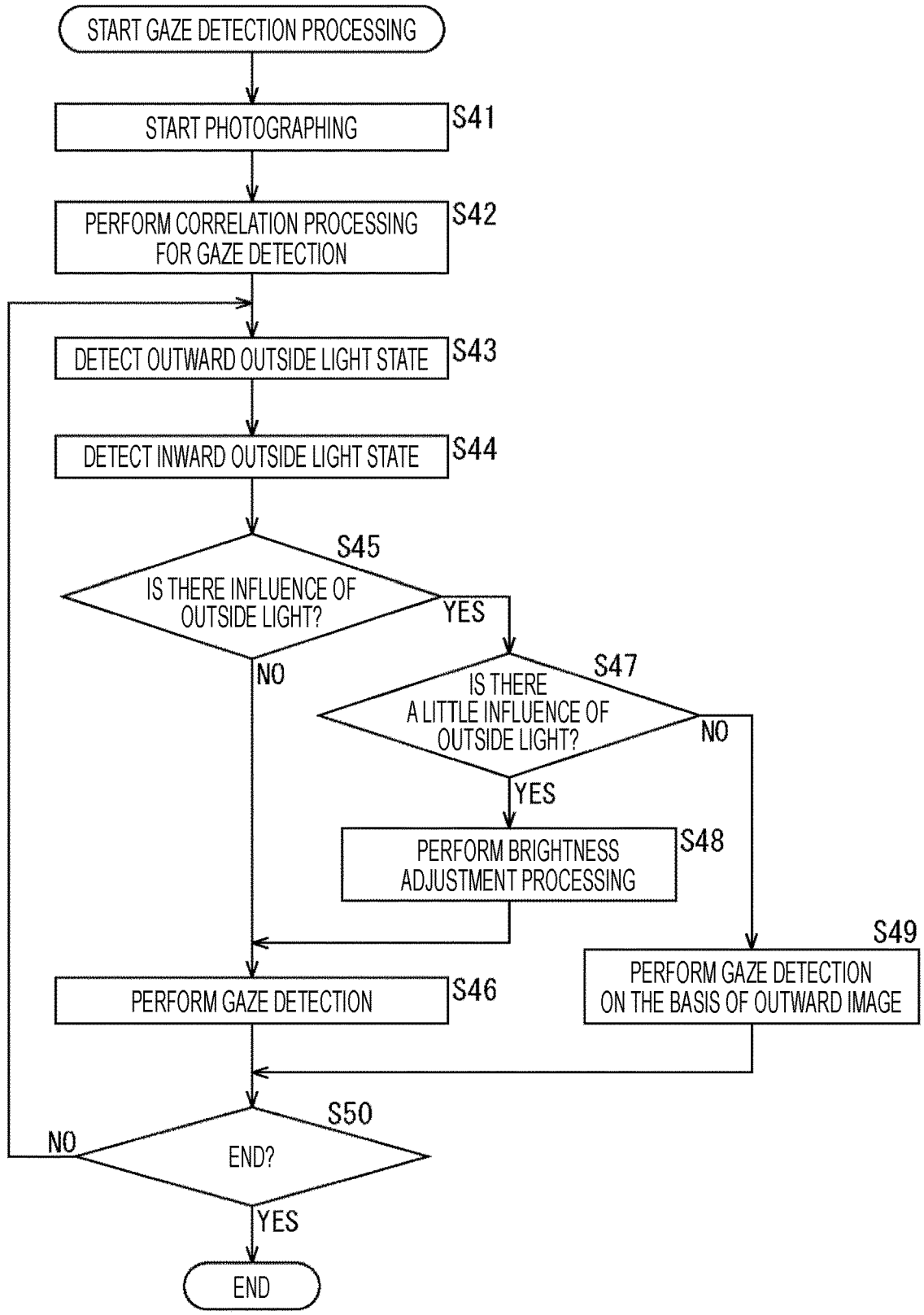
FIG. 7 is a flowchart for describing gaze detection processing.

Next, the gaze detection processing performed by the image processing device 11 will be described with reference to a flowchart in FIG. 7. This gaze detection processing is performed, for example, when an application program using a gaze direction of a user is activated in the image processing device 11.

The outward camera 21 and the inward camera 22 start photographing in step S41. In step S41, processing similar to that in step S11 in FIG. 6 is performed, and photographing of an outward image and an inward image is started. Also, the host control unit 87 controls the infrared ray transmission unit 23 to emit an infrared ray to a user.

In step S42, the image processing device 11 performs correlation processing for gaze detection.

Figure 6:
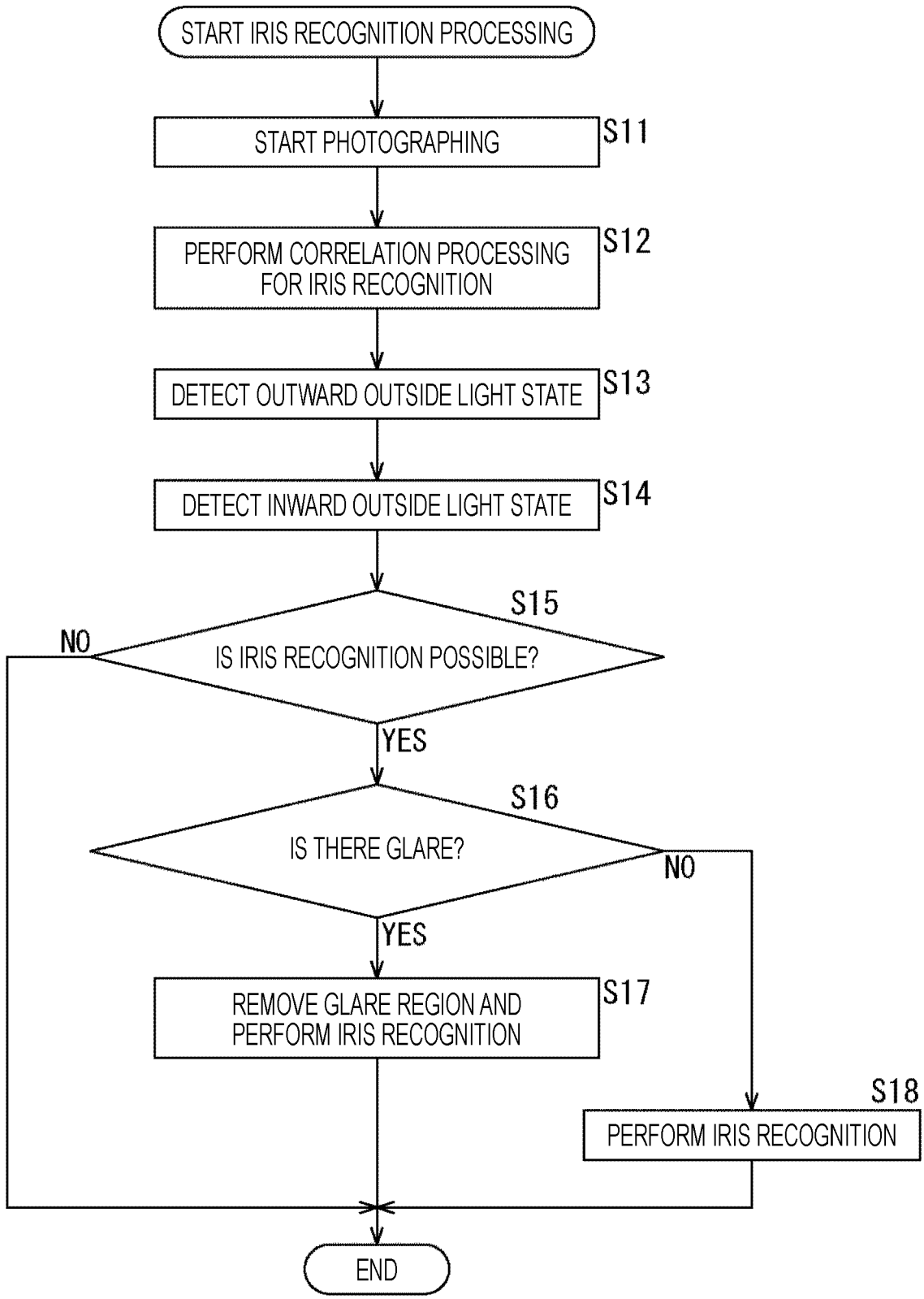
FIG. 6 is a flowchart for describing iris recognition processing.

For example, the outward state detection unit 92 generates an outward brightness map by performing processing similar to the processing in step S12 in FIG. 6, and outputs this as a detection result of an outward outside light state to the host control unit 87. Here, for example, a size of each divided region of a case where the outward image is divided into a plurality of divided regions may be set to be larger than that in generation of an outward brightness map in the correlation processing for iris recognition in step S12 in FIG. 6.

Also, the inward state detection unit 101 generates an inward brightness map by performing processing similar to the processing in step S12 in FIG. 6, and supplies this as a detection result of an inward outside light state to the host control unit 87. In a case of the inward brightness map, for example, a size of each divided region of a case where the inward image is divided into a plurality of divided regions may be set to be larger than that in generation of an inward brightness map in the correlation processing for iris recognition in step S12 in FIG. 6.

The host control unit 87 associates the outward brightness map supplied by the outward state detection unit 92 and the inward brightness map supplied by the inward state detection unit 101 and holds these as correlation information for gaze detection. The correlation information for gaze detection acquired in such a manner is information indicating a correlation between brightness of the outward image and that of the inward image.

It can be said that the correlation processing for gaze detection in the above manner in which processing the correlation information for gaze detection is calculated and held is processing of performing calibration for detection of an outside light state. More specifically, for example, the correlation processing for gaze detection is performed at timing at which a user wears the image processing device 11.

After the correlation processing for gaze detection is performed, processing in step S43 and step S44 is performed at timing at which detection of a gaze of a user is started. However, since these kinds of processing are similar to the processing in step S13 and step S14 in FIG. 6, a description thereof is omitted.

In step S45, the host control unit 87 determines whether there is an influence of outside light in performance of the gaze detection on the basis of the detection result of the outward outside light state which result is acquired in step S43 and the detection result of the inward outside light state which result is acquired in step S44.

For example, the host control unit 87 determines that there is not an influence of outside light in a case where an outside light state level acquired in step S44 is the level L0 and brightness of the outward image is brightness equal to or lower than a certain level on the basis of an outward brightness map acquired in step S43.

For example, on the basis of a histogram of each divided region in the outward brightness map, an average value or a representative value of luminance (brightness) in each divided region is calculated as brightness of the divided region, and an average value, a representative value, an integration value, or the like of brightness of all divided regions is calculated as brightness of the outward image.

Here, there being an influence of outside light means a case where there is an influence of outside light in a degree in which gaze detection cannot be performed correctly if an inward image is used as it is. Note that determination whether there is an influence of outside light is not limited to the example described here, and only needs to be performed on the basis of whether an outside light state indicated by an outward brightness map, an inward brightness map, an outside light state level, or the like satisfies a predetermined condition.

In a case where it is determined in step S45 that there is no influence of outside light, the recognition processing unit 102 performs gaze detection on the basis of an inward image supplied by the signal processing unit 84 and outputs a result of the detection in step S46.

For example, the recognition processing unit 102 detects, by image recognition or the like, a region of an infrared ray emitted to a user by the infrared ray transmission unit 23, that is, a bright spot of the infrared ray, and a pupil of the user from the inward image. Then, the recognition processing unit 102 detects a gaze direction of the user on the basis of a positional relationship between one or a plurality of detected bright spots of an infrared ray and a detected pupil of the user in the inward image, and sets the gaze direction as a detection result of the gaze detection.

After the gaze detection is performed, the processing goes to step S50.

On the other hand, in a case where it is determined in step S45 that there is an influence of outside light, the host control unit 87 determines in step S47 whether there is a little influence of the outside light.

That is, the host control unit 87 determines whether there is a little influence of the outside light on the basis of the detection result of the outward outside light state which result is acquired in step S43, the detection result of the inward outside light state which result is acquired in step S44, and the held correlation information for gaze detection. Here, there being a little influence of outside light means that there is a little influence of the outside light with respect to gaze detection in a degree in which the gaze detection can be performed by performance of brightness adjustment processing (described later).

For example, the host control unit 87 specifies whether a relationship between a luminance distribution indicated by the outward brightness map acquired in step S43 and a luminance distribution indicated by the inward brightness map acquired in step S44 is similar to a relationship between a luminance distribution indicated by an outward brightness map and a luminance distribution indicated by an inward brightness map which maps are correlation information for gaze detection, that is, whether there is a correlation in the luminance distribution.

In other words, in a case where the luminance distribution of the outward brightness map acquired in step S43 and the luminance distribution of the outward brightness map as the correlation information for gaze detection are the same and the luminance distribution of the inward brightness map acquired in step S44 and the luminance distribution of the inward brightness map as the correlation information for gaze detection are the same, it is determined that there is a correlation in the luminance distribution.

In a case where there is a correlation in the luminance distribution and the outside light state level as the detection result of the inward outside light state which result is acquired in step S44 is the level L0 or the level L1, the host control unit 87 determines that there is a little influence of the outside light.

Note that determination whether there is a little influence of outside light only needs to be performed by specification whether a predetermined condition is satisfied according to the detection result of the outward outside light state which result is acquired in step S43, the detection result of the inward outside light state which result is acquired in step S44, and the held correlation information for gaze detection. That is, determination whether there is a little influence of outside light is not limited to the example described here and only needs to be performed by determination whether a state of outside light which state is indicated by, for example, a detection result of an outward outside light state or a detection result of an inward outside light state satisfies a predetermined condition.

In a case where it is determined in step S47 that there is a little influence of outside light, the host control unit 87 performs brightness adjustment processing in step S48 on the basis of at least one of the detection result of the outward outside light state which result is acquired in step S43 and the detection result of the inward outside light state which result is acquired in step S44. Here, the brightness adjustment processing is processing related to brightness of an inward image, that is, processing of adjusting brightness of an inward image.

More specifically, for example, the host control unit 87 controls the infrared ray transmission unit 23 to turn on/off the infrared ray transmission unit 23 or to adjust an emission amount (light quantity) of an infrared ray as the brightness adjustment processing. That is, the host control unit 87 changes an infrared ray transmission unit 23 to be turned on, changes the number of infrared ray transmission units 23 to be turned on, or changes a quantity of an infrared ray emitted by an infrared ray transmission unit 23.

More specifically, in a case where an infrared ray emitted by a predetermined infrared ray transmission unit 23 is reflected in a bright region in an inward image, that is, in a case where a bright spot of the infrared ray is in a region of predetermined brightness or higher which region is calculated from a detection result of an inward outside light state, the host control unit 87 controls the infrared ray transmission unit 23 in such a manner that a quantity of the infrared ray is increased. With this arrangement, it becomes possible to more correctly specify a bright spot of an infrared ray even in a bright region in an inward image and to reduce an influence of outside light.

Also, for example, in a case where an infrared ray emitted by the infrared ray transmission unit 23 is reflected in a region of predetermined brightness or higher in an inward image, the host control unit 87 may stop emission of the infrared ray by the infrared ray transmission unit 23 that outputs the infrared ray, or may make a different infrared ray transmission unit 23 emit an infrared ray in such a manner that the infrared ray is reflected in a region having brightness lower than the predetermined brightness in the inward image. In such a manner, it is possible to reduce an influence of outside light by changing turning on/off of an infrared ray transmission unit 23 or an emission position of an infrared ray. Also, it is possible to reduce power consumption by turning off the infrared ray transmission unit 23 in such a manner that an infrared ray is not emitted to an object part corresponding to a region of brightness with which detection of a bright spot of the infrared ray is difficult.

Here, a region in an inward image which region is excluded from an emission object of an infrared ray or is set to be an object of a quantity increase of an infrared ray may be, for example, a region of predetermined brightness or higher which region is specified only from a detection result of an inward outside light state or may be a region specified by utilization of not only a detection result of an inward outside light state but also a detection result of an outward outside light state or estimated glare region information. For example, it is possible to effectively reduce an influence of outside light by making a bright spot of an infrared ray clearer in an estimated glare region indicated by estimated glare region information acquired in iris recognition processing or by excluding the estimated glare region from an object of infrared ray emission.

Moreover, for example, as brightness adjustment processing, the host control unit 87 may control the control unit 85 to change a photometric method.

For example, it is considered that a photometric method is changed to a spot photometric method in a case where there is a bright region in an outward image, and a region in an inward image which region has a correlation with the bright region is also bright and a position of the region is in the vicinity of an end of the inward image according to detection results of an outward outside light state and an inward outside light state. Here, the spot photometric method is a photometric method of deciding, according to luminance information (luminance level) only in a region near a center in an inward image, brightness information such as exposure time, or gain in a gain adjustment or a parameter of a contrast adjustment with respect to the whole inward image.

In this case, for example, the control unit 85 decides brightness information by the spot photometric method on the basis of a luminance level of a region in the vicinity of a center of an inward image supplied by the signal processing unit 84. Then, the control unit 85 makes the inward camera 22 perform photographing according to exposure time as the decided brightness information, or makes the signal processing unit 84 perform gain adjustment processing or contrast adjustment processing with respect to an inward image output to the inward image processing unit 86 according to gain or a parameter as the brightness information.

With this arrangement, it is possible to make a bright spot of an infrared ray or a pupil in an inward image be reflected clearly with more appropriate brightness by changing exposure time to shorter time or appropriately changing gain of a gain adjustment or a parameter of a contrast adjustment and to reduce an influence of outside light.

After the brightness adjustment processing is performed in the above manner, the processing goes to step S46 and the above-described gaze detection is performed. In this case, since gaze detection is performed on the basis of an inward image acquired by performance of the brightness adjustment, that is, an inward image photographed after the brightness adjustment processing is performed, it is possible to reduce an influence of outside light and to more correctly detect a gaze direction of a user.

Also, in a case where it is not determined in step S47 that an influence of outside light is a little, that is, in a case where it is not possible to detect a gaze direction sufficiently accurately from an inward image due to an influence of outside light, the processing goes to step S49.

In step S49, the host control unit 87 performs gaze detection on the basis of an outward image. That is, the optical flow calculation unit 93 calculates an optical flow on the basis of an outward image supplied by the signal processing unit 81 and supplies a result of the calculation to the host control unit 87. Also, the host control unit 87 calculates movement of the outward camera 21 on the basis of the optical flow supplied by the optical flow calculation unit 93, calculates a gaze direction of a user with the movement as movement of a gaze of the user, and outputs a result of the calculation as a result of the gaze detection.

The optical flow detected from the outward image indicates movement of an object. Also, when the user starts moving the gaze, a head of the user, that is, the outward camera 21 also often moves in a direction in which the gaze changes. Thus, by considering that movement of the object in the outward image is generated by movement of the outward camera 21, that is, a change in a photographing direction of the outward camera 21, it is possible to detect approximate movement of the gaze of the user from the optical flow.

In a case where an influence of outside light is significant and detection of a gaze of a user from an inward image is difficult, it is possible to continuously perform gaze detection by temporarily using, as a result of the gaze detection, a gaze direction of the user which direction is calculated from an optical flow. That is, it is possible to continuously follow a gaze.

After the gaze direction of the user is detected from the optical flow in such a manner, the processing goes to step S50.

If the gaze detection is performed in step S49 or step S46, the host control unit 87 determines in step S50 whether to end the processing. For example, it is determined to end the processing in a case where it is instructed to end an application program using gaze detection and the gaze detection is ended.

In a case where it is determined in step S50 not to end the processing, the processing goes back to step S43 and the above-described processing is repeatedly performed. On the other hand, in a case of being determined in step S50 to be ended, the gaze detection processing is ended.

In the above manner, the image processing device 11 performs gaze detection after arbitrarily performing brightness adjustment processing according to detection results of an outward outside light state and an inward outside light state. In such a manner, it is possible to reduce an influence of outside light by arbitrarily performing brightness adjustment processing according to a state of the outside light and to more correctly detect a gaze of a user.

Note that brightness adjustment processing may be also arbitrarily performed in the iris recognition processing described with reference to FIG. 6. In this case, by the brightness adjustment processing, it is possible to increase a region of an inward image which region can be used for iris recognition, that is, a recognizable region.

Also, a case of applying the present technology to a glasses-type wearable device has been described in the above. However, the present technology can be also applied to a system or an electronic device that includes a plurality of photographing units, which are an inward camera that photographs an inward image with a user side as an inward side and an outward camera that photographs an outward image with an opposite side of the user side as an outward side, and that is, for example, a personal computer that performs iris recognition or gaze detection of a user by a web camera or the like as an inward camera.

Incidentally, the above-described series of processing can be executed by hardware or by software. In a case where the series of processing is executed by software, a program included in the software is installed into a computer. Here, the computer includes a computer embedded in special hardware or a general personal computer that can execute various functions by installation of various programs, for example.

Figure 8:
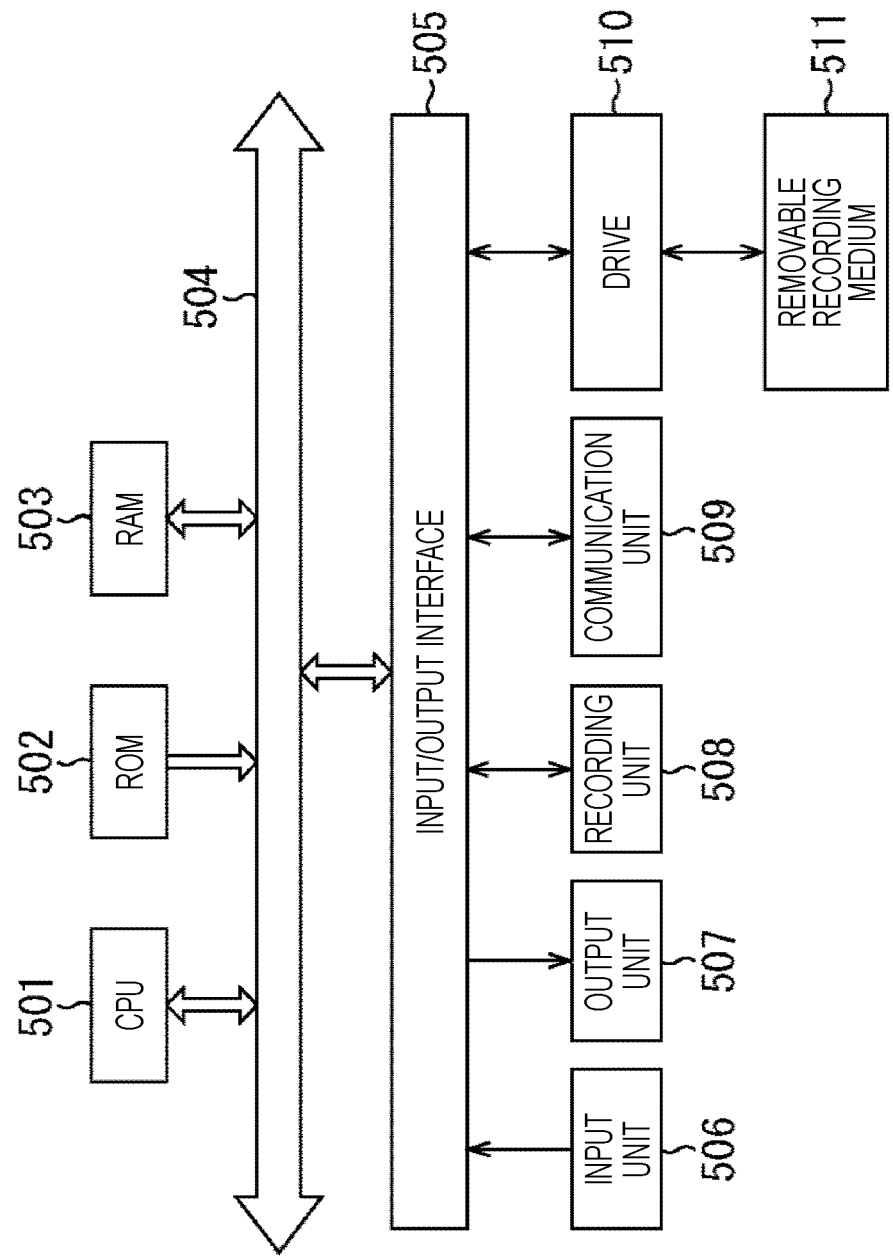
FIG. 8 is a view illustrating a configuration example of a computer.

FIG. 8 is a block diagram illustrating a configuration example of hardware of a computer that executes the above-described series of processing by a program.

In a computer, a central processing unit (CPU) 501, a read only memory (ROM) 502, and a random access memory (RAM) 503 are connected to each other by a bus 504.

An input/output interface 505 is further connected to the bus 504. To the input/output interface 505, an input unit 506, an output unit 507, a recording unit 508, a communication unit 509, and a drive 510 are connected.

The input unit 506 includes a keyboard, a mouse, a microphone, an imaging element, or the like. The output unit 507 includes a display, a speaker, or the like. The recording unit 508 includes a hard disk, a nonvolatile memory, or the like. The communication unit 509 includes a network interface or the like. The drive 510 drives a removable recording medium 511 such as a magnetic disk, an optical disk, a magneto optical disk, or a semiconductor memory.

In the computer configured in the above manner, for example, the CPU 501 loads a program recorded in the recording unit 508 into the RAM 503 through the input/output interface 505 and the bus 504 and executes the program, whereby the above-described series of processing is performed.

For example, the program executed by the computer (CPU 501) can be recorded in the removable recording medium 511 as a package medium or the like and provided. Also, the program can be provided through a wired or wireless transmission medium such as a local area network, the Internet, or a digital satellite broadcast.

In the computer, the program can be installed into the recording unit 508 through the input/output interface 505 by mounting the removable recording medium 511 to the drive 510. Also, the program can be received in the communication unit 509 through a wired or wireless transmission medium and can be installed into the recording unit 508. In addition, the program can be previously installed in the ROM 502 or the recording unit 508.

Note that a program executed by the computer may be a program in which processing is performed in time series in order described in the present description or may be a program in which processing is performed in parallel or at necessary timing such as at performance of a call.

Also, an embodiment of the present technology is not limited to the above-described embodiments and various modifications can be made within the spirit and the scope of the present technology.

For example, the present technology may include a configuration of cloud computing in which one function is divided by a plurality of devices through a network and processing is performed in cooperation.

Also, each step described in the above flowchart can be executed by one device or can be divided and executed by a plurality of devices.

Moreover, in a case where a plurality of kinds of processing is included in one step, the plurality of kinds of processing included in the one step can be executed by one device or can be divided and executed by a plurality of devices.

Moreover, the present technology can include the following configurations.

(1) An image processing device including:
an inward state detection unit that detects, on the basis of an inward image acquired by photographing of a user side, a state of outside light in the inward image as an inward outside light state;
an outward state detection unit that detects, on the basis of an outward image acquired by photographing of an opposite side of the user side, a state of outside light in the outward image as an outward outside light state;
a control unit that performs brightness adjustment processing related to brightness of the inward image according to a detection result of the inward outside light state and a detection result of the outward outside light state; and
a recognition processing unit that performs gaze detection of the user on the basis of the inward image acquired by performance of the brightness adjustment processing.

(2) The image processing device according to (1),
in which the control unit performs the brightness adjustment processing in a case where a state of outside light which state is indicated by the detection result of the inward outside light state and the detection result of the outward outside light state satisfies a first condition.

(3) The image processing device according to (1) or (2),
in which the control unit changes a photometric method in the brightness adjustment processing.

(4) The image processing device according to (1) or (2),
in which the control unit changes exposure time of the inward image in the brightness adjustment processing.

(5) The image processing device according to (1) or (2),
in which the control unit changes gain of gain adjustment processing performed with respect to the inward image in the brightness adjustment processing.

(6) The image processing device according to any one of (1) to (5),
in which the inward image is an infrared image, and
the image processing device further includes one or a plurality of infrared ray transmission units that emits an infrared ray to the user.

(7) The image processing device according to (6),
in which the control unit changes the infrared ray transmission unit to be turned on in the brightness adjustment processing.

(8) The image processing device according to (6) or (7),
in which the control unit changes the number of the infrared ray transmission units to be turned on in the brightness adjustment processing.

(9) The image processing device according to any one of (6) to (8),
in which the control unit changes a quantity of the infrared ray, which is emitted by the infrared ray transmission unit, in the brightness adjustment processing.

(10) The image processing device according to any one of (1) to (9),
in which the control unit performs gaze detection of the user on the basis of the outward image in a case where a state of outside light which state is indicated by the detection result of the inward outside light state and the detection result of the outward outside light state satisfies a second condition.

(11) The image processing device according to any one of (1) to (10),
in which the recognition processing unit performs iris recognition on the basis of the inward image.

(12) The image processing device according to (11),
in which the control unit specifies a glare region of the outside light in the inward image on the basis of the detection result of the inward outside light state and the detection result of the outward outside light state, and
the recognition processing unit performs the iris recognition while excluding the glare region from the inward image.

(13) An image processing method including the steps of:
detecting, on the basis of an inward image acquired by photographing of a user side, a state of outside light in the inward image as an inward outside light state;
detecting, on the basis of an outward image acquired by photographing of an opposite side of the user side, a state of outside light in the outward image as an outward outside light state;
performing brightness adjustment processing related to brightness of the inward image according to a detection result of the inward outside light state and a detection result of the outward outside light state; and
performing gaze detection of the user on the basis of the inward image acquired by performance of the brightness adjustment processing.

(14) A program causing a computer to execute processing including the steps of:
detecting, on the basis of an inward image acquired by photographing of a user side, a state of outside light in the inward image as an inward outside light state;
detecting, on the basis of an outward image acquired by photographing of an opposite side of the user side, a state of outside light in the outward image as an outward outside light state;
performing brightness adjustment processing related to brightness of the inward image according to a detection result of the inward outside light state and a detection result of the outward outside light state; and
performing gaze detection of the user on the basis of the inward image acquired by performance of the brightness adjustment processing.

REFERENCE SIGNS LIST

11 Image processing device
21 Outward camera
22-R, 22-L, 22 Inward camera
23-1 to 23-12, 23 Infrared ray transmission unit
83 Outward image processing unit
86 Inward image processing unit
87 Host control unit
92 Outward state detection unit
93 Optical flow calculation unit
101 Inward state detection unit
102 Recognition processing unit

The invention claimed is:

1. An image processing device comprising:
an inward state detection unit that detects, on the basis of an inward image acquired by photographing of a user side, a state of outside light in the inward image as an inward outside light state;
an outward state detection unit that detects, on the basis of an outward image acquired by photographing of an opposite side of the user side, a state of outside light in the outward image as an outward outside light state;
a control unit that performs brightness adjustment processing related to brightness of the inward image according to a detection result of the inward outside light state and a detection result of the outward outside light state; and a recognition processing unit that performs gaze detection of the user on the basis of the inward image acquired by performance of the brightness adjustment processing.

2. The image processing device according to claim 1, wherein the control unit performs the brightness adjustment processing in a case where a state of outside light which state is indicated by the detection result of the inward outside light state and the detection result of the outward outside light state satisfies a first condition.

3. The image processing device according to claim 1, wherein the control unit changes a photometric method in the brightness adjustment processing.

4. The image processing device according to claim 1, wherein the control unit changes exposure time of the inward image in the brightness adjustment processing.

5. The image processing device according to claim 1, wherein the control unit changes gain of gain adjustment processing performed with respect to the inward image in the brightness adjustment processing.

6. The image processing device according to claim 1, wherein the inward image is an infrared image, and the image processing device further comprises one or a plurality of infrared ray transmission units that emits an infrared ray to the user.

7. The image processing device according to claim 6, wherein the control unit changes the infrared ray transmission unit to be turned on in the brightness adjustment processing.

8. The image processing device according to claim 6, wherein the control unit changes the number of the infrared ray transmission units to be turned on in the brightness adjustment processing.

9. The image processing device according to claim 6, wherein the control unit changes a quantity of the infrared ray, which is emitted by the infrared ray transmission unit, in the brightness adjustment processing.

10. The image processing device according to claim 1, wherein the control unit performs gaze detection of the user on the basis of the outward image in a case where a state of outside light which state is indicated by the detection result of the inward outside light state and the detection result of the outward outside light state satisfies a second condition.

11. The image processing device according to claim 1, wherein the recognition processing unit performs iris recognition on the basis of the inward image.

12. The image processing device according to claim 11, wherein the control unit specifies a glare region of the outside light in the inward image on the basis of the detection result of the inward outside light state and the detection result of the outward outside light state, and the recognition processing unit performs the iris recognition while excluding the glare region from the inward image.

13. An image processing method comprising the steps of:
detecting, on the basis of an inward image acquired by photographing of a user side, a state of outside light in the inward image as an inward outside light state;
detecting, on the basis of an outward image acquired by photographing of an opposite side of the user side, a state of outside light in the outward image as an outward outside light state;
performing brightness adjustment processing related to brightness of the inward image according to a detection result of the inward outside light state and a detection result of the outward outside light state; and
performing gaze detection of the user on the basis of the inward image acquired by performance of the brightness adjustment processing.

14. A non-transitory computer-readable medium having stored thereon, computer-readable instructions, which when executed by a computer, causes the computer to execute operations, the operations comprising:
detecting, on the basis of an inward image acquired by photographing of a user side, a state of outside light in the inward image as an inward outside light state;
detecting, on the basis of an outward image acquired by photographing of an opposite side of the user side, a state of outside light in the outward image as an outward outside light state;
performing brightness adjustment processing related to brightness of the inward image according to a detection result of the inward outside light state and a detection result of the outward outside light state; and
performing gaze detection of the user on the basis of the inward image acquired by performance of the brightness adjustment processing.

* * * * *